(12) United States Patent
Gronberg et al.

(10) Patent No.: US 6,573,291 B2
(45) Date of Patent: Jun. 3, 2003

(54) METHOD AND USE

(75) Inventors: Alvar Gronberg, Knivsta (SE); Jerry R. Colca, Kalamazoo, MI (US)

(73) Assignee: Biovitrum AB, Stockholm (SE)

( * ) Notice: Subject to any disclaimer, the term of this patent is extended or adjusted under 35 U.S.C. 154(b) by 0 days.

(21) Appl. No.: 10/006,518

(22) Filed: Dec. 3, 2001

(65) Prior Publication Data
US 2002/0107277 A1 Aug. 8, 2002

Related U.S. Application Data
(60) Provisional application No. 60/254,701, filed on Dec. 11, 2000.

(30) Foreign Application Priority Data
Dec. 4, 2000 (SE) ................................................. 0004462

(51) Int. Cl.⁷ ............................................. A61K 31/415
(52) U.S. Cl. ...................................... 514/407; 514/884
(58) Field of Search ................................... 514/407, 884

(56) References Cited

U.S. PATENT DOCUMENTS 6,291,476 B1 * 9/2001 Kordik et al. ............... 514/310

FOREIGN PATENT DOCUMENTS

| EP | 0 142 190 | 5/1985 | .......... C07D/233/26 |
| WO | WO 93/03714 | 3/1993 | ........... A61K/31/11 |
| WO | WO 00/69849 | 11/2000 | .......... C07D/401/12 |

OTHER PUBLICATIONS

STN International, File CAPLUS accession No. 1999:382989, Document No. 131:165408, Meurer, Janet A., et al. "Properties of native and in vitro glucosylated forms of the glucagon–like peptide–1 receptor antagonist exending(9–39)", Metab., Clin. Exp. (1999), 48(6), pp. 716–724.

* cited by examiner

Primary Examiner—Kevin E. Weddington
(74) Attorney, Agent, or Firm—Fish & Richardson PC

(57) ABSTRACT

The invention relates to a method of antagonizing GLP-1 activity in a mammalian patient, comprising administering to said patient an effective amount of a compound of the general formula I:

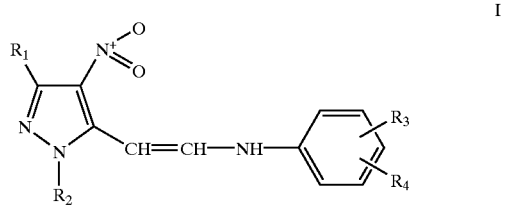

wherein
$R_1$ and $R_2$ independently of each other are $C_{1-4}$alkyl,
$R_3$ is halogen, hydroxy, $C_{1-4}$-alkoxy or trifluoromethoxy,
$R_4$ is hydrogen, hydroxy or $C_{1-4}$-alkoxy,
or a pharmacologically acceptable salt thereof. The invention also relates to a pharmaceutical composition comprising a compound of formula I.

20 Claims, 3 Drawing Sheets

METHOD AND USE

CROSS REFERENCE TO RELATED APPLICATIONS

This application claims priority to Swedish Patent Application No. 0004462-8, filed Dec. 4, 2000, and U.S. Provisional Patent Application Serial No. 60/254,701, filed Dec. 11, 2000. These applications are incorporated herein by reference in their entirety.

FIELD OF THE INVENTION

The present invention relates to the use of selected compounds to antagonize or inhibit GLP-1 activity in a mammal patient in need thereof, as well as to a pharmaceutical composition comprising such antagonist(s).

BACKGROUND OF THE INVENTION

Glucagon-like peptide 1(7–36)amide (GLP-1) is an intestinal hormone and neurotransmitter that is involved in the control of metabolism and food intake. A major function of the hormone appears to be the regulation of the amount of insulin released in response to a meal, GLP-1 increasing the insulin secretion. It has therefore been proposed that a molecule capable of augmenting the action of GLP-1, i.e. a GLP-1 agonist, should be useful as an antidiabetic agent to lower elevated blood glucose levels in a mammal serum.

Conversely, a GLP-1 antagonist could be used to elevate the blood glucose level in a subject afflicted with too low a blood glucose level. An exemplary such condition is postprandial reactive hypoglycemia, such as in partially gastrorectomised subjects (Toft-Nielsen M. et al., Diabetologia 41(10):1180–6, 1998). Other disorders where a GLP-1 antagonist is believed to be useful include anorexia (Jensen P. B. et al., J. Clin. Invest. 102(2):503–10, 1998), and reduced intestinal motility and constipation (Tolessa T. et al., Digestive diseases and Sciences 43(10):2284–99, 1998). It has also been suggested that a GLP-1 antagonist could be used to reduce symptoms in Alzheimer's disease, GLP-1 mediating the inhibition of beta-amyloid induced neural activation (Oka J. I. et al., SO Neuroreport 10(8):1643–6, 1999).

SUMMARY OF THE INVENTION

According to the present invention, a limited class of chemical compounds have been found which are excellent antagonists of GLP-1 and therefore would be useful for the treatment of diseases or disorders where inhibition of GLP-1 action would be indicated.

Therefore, in one aspect thereof, the present invention provides a method of antagonizing (e.g., inhibiting) GLP-1 activity in a mammalian patient, comprising administering to said patient an effective amount of a compound of the general formula I:

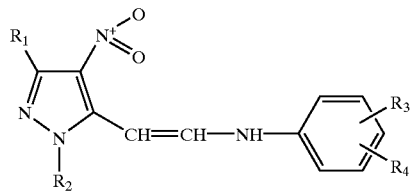

wherein:
$R_1$ and $R_2$ independently of each other are $C_{1-4}$alkyl,
$R_3$ is halogen, hydroxy, $C_{1-4}$-alkoxy or trifluoromethoxy, and
$R_4$ is hydrogen, hydroxy or $C_{1-4}$-alkoxy,
or a pharmacologically acceptable salt thereof.

In another aspect, the present invention provides a compound of formula I above for use as a pharmaceutical.

In still another aspect, the present invention provides a pharmaceutical composition comprising a compound of formula I above and optionally a pharmaceutically acceptable carrier.

Yet another aspect of the present invention provides the use of a compound of formula I above for the preparation of a medicament for antagonizing GLP-1 activity in a mammalian patient.

This invention also features a method of treating a disorder where inhibition of GLP-1 activity is indicated. The method includes administering to a mammal subject in need thereof an effective amount of a compound of formula I above.

Further, this invention features a method of treating a disorder where inhibition of GLP-1 activity is indicated. The method includes administering to a mammal subject in need thereof a pharmaceutical composition, wherein the pharmaceutical composition includes an effective amount of a compound of formula I above and a pharmaceutically acceptable carrier.

Also within the scope of this invention is a method for the manufacture of a medicament for antagonizing GLP-1 activity in a mammalian patient, characterized in that a compound of formula I above is used as the pharmaceutically active substance.

DETAILED DESCRIPTION OF THE INVENTION

Figure 1:
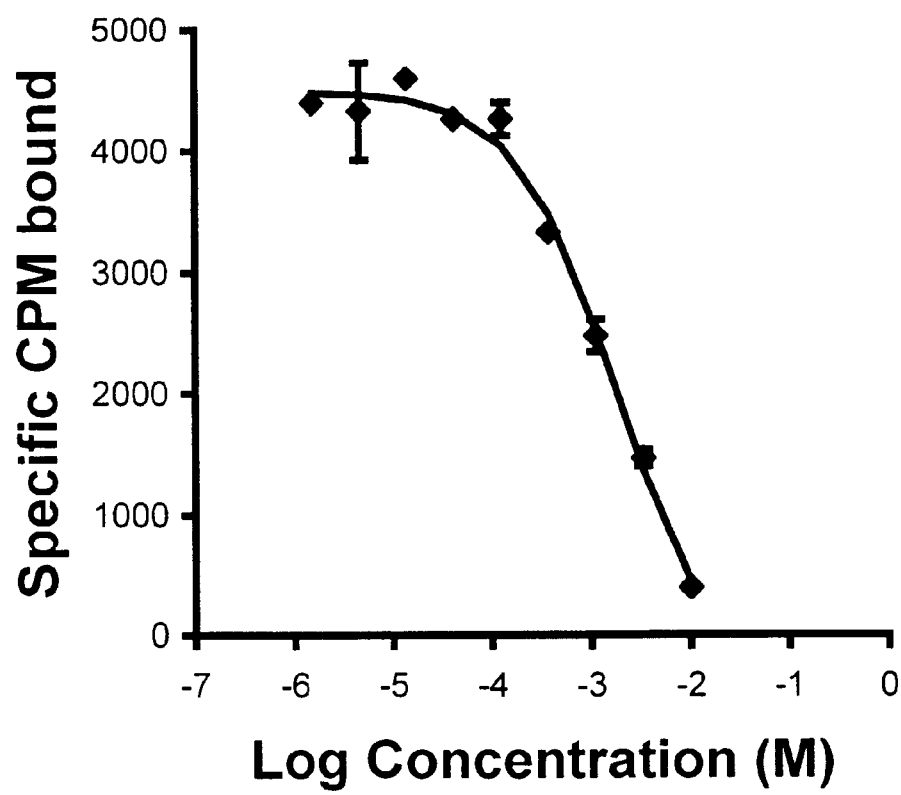
FIG. 1 is a diagram showing binding (cpm) of radiolabeled GLP-1 to a preparation of GLP-1 receptors in the presence of different concentrations (M) of the antagonist compound A.

As mentioned above, the invention resides in the finding of a limited class of compounds, i.e. compounds of formula I above, that are GLP-1 antagonists and which could therefore be used as GLP-1 antagonists for the treatment of a mammal subject, especially a human being (but also an animal, e.g. a pet), in need of such treatment. Disorders where administration of a GLP-1 antagonist would be indicated include, for example, postprandial reactive hypoglycemia, anorexia, reduced intestinal motility and constipation, and Alzheimer's disease.

In the compounds of formula I, $R_1$ and $R_2$ are preferably methyl. $R_3$ is preferably halogen, hydroxy, methoxy or trifluoromethoxy. $R_4$ is preferably hydrogen, hydroxy or methoxy. Halogen is especially fluoro or chloro.

Specific compounds of the invention are:

4-chloro-2-{[(E)-2-(1,3-dimethyl-4-nitro-1H-pyrazol-5-yl)ethenyl]amino}phenol;
4-fluoro-1-{[(E)-2-(1,3-dimethyl-4-nitro-1H-pyrazol-5-yl)ethenyl]amino}benzene;
4-trifluoromethoxy-1-{[(E)-2-(1,3-dimethyl-4-nitro-1H-pyrazol-5-yl)ethenyl]amino}benzene; and
2,4-dimethoxy-1-{[(E)-2-(1,3-dimethyl-4-nitro-1H-pyrazol-5-yl)ethenyl]amino}benzene.

The compounds of formula I may be used as the compounds as such or, where appropriate, as the pharmacologically acceptable salts (acid or base addition salts) thereof. The compounds covered by formula I are also meant to include stereochemically isomeric forms thereof, including optical isomers, such as enantiomers and racemates. Such compounds can also occur as cis- or trans-, E- or Z-double bond isomeric forms. All of the just-described isomeric forms are contemplated.

The pharmacologically acceptable addition salts as mentioned above are meant to comprise the therapeutically active non-toxic acid and base addition salt forms which the compounds are able to form. Compounds which have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

The compounds of formula I can be brought into suitable galenic forms, such as compositions for oral use, for injection, for nasal spray administration or the like, in accordance with accepted pharmaceutical procedures. Such pharmaceutical compositions according to the invention comprise an effective amount of one, or optionally more, compound(s) of formula I in association with compatible pharmaceutically acceptable carrier materials, or diluents, as are well known in the art. The carriers may be any inert material, organic or inorganic, suitable for oral enteral, rectal, percutaneous, subcutaneous or parenteral administration, such as: water, gelatin, gum arabicum, lactose, microcrystalline cellulose, starch, sodium starch glycolate, calcium hydrogen phosphate, magnesium stearate, talcum, colloidal silicon dioxide, and the like. Such compositions may also contain other pharmacologically active agents, and conventional additives, such as stabilizers, wetting agents, emulsifiers, flavouring agents, buffers, and the like.

The compositions according to the invention can e.g. be made up in solid or liquid form for oral administration, such as tablets, pills, capsules, powders, syrups, elixirs, dispersable granules, cachets, suppositories and the like, in the form of sterile solutions, suspensions or emulsions for parenteral administration, sprays, e.g. a nasal spray, transdermal preparations, e.g. patches, and the like.

This invention relates to a method of treating a disorder where inhibition of GLP-1 activity is indicated. The method includes administering to a mammal subject (e.g., human) in need thereof an effective amount of one or more compounds of formula I above. The disorder includes, but is not limited to, postprandial reactive hypoglycemia, anorexia, reduced intestinal motility and constipation, and Alzheimer's disease.

"An effective amount" refers to an amount of a compound which confers a therapeutic effect on the treated subject. The therapeutic effect may be objective (i.e., measurably by some test or marker) or subjective (i.e., subject gives an indication of or feels an effect). The dose level of the compounds of formula I, and the frequency of dosage of the specific combination, will vary depending on a variety of factors including the potency of each specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 150 mg per kilo of body weight, preferably from about 0.01 mg to about 100 mg per kilo of body weight, especially from about 0.1 to about 50 mg per kilo of body weight the compound of formula I, administered singly or multiply in doses, e.g. dosages of from about 0.01 mg to about 25 mg each. Usually, such a combined dosage is given orally but e.g. parenteral or rectal administration may also be chosen. A currently preferred oral daily dosage for a human subject is from about 1 to about 80 mg, preferably from about 1 to about 50 mg per day.

Several of the compounds of formula I above are commercially available. Generally, compounds of formula I may be prepared by various routes as described in the following exemplary method schemes where "R1" denotes the terminal $R_3/R_4$-substituted phenyl group in the structural formula I above, and $R_1$ and $R_2$ in formula I both are methyl.

Method 1

Displacement of X (X=e.g. Cl) in starting compound (A) in the reaction scheme below with an enamine gives compound (B) (similar to the displacement with cyanide described in Tet. (1979) 35; 1331). Treatment of (B) with an excess of a variety of enamines leads to analogues (C).

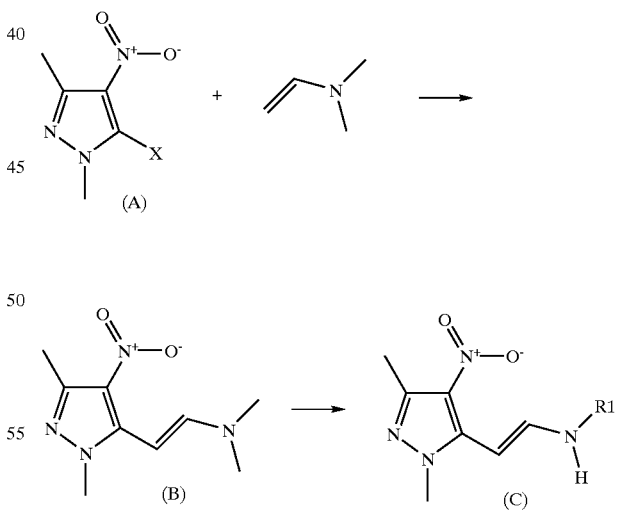

Method 2

Starting compound (D) in the reaction scheme below is subjected to a Michael type addition with the mono-anion of malonic diesters (J C S Perkin I, (1991)5; 1077). Subsequent decarboxylation to give the corresponding acetic acid derivative and conversion thereof using standard methods gives the aldehyde (E) which by reaction with a suitable amine gives the desired analogue (C).

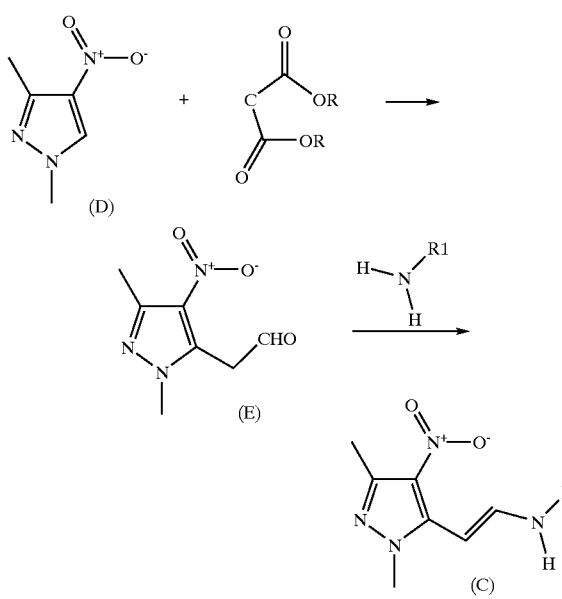

(D)

(E)

(C)

Method 3

Starting compound (D) is reacted as shown in reaction scheme below to give the acetonitrile intermediate (Pol. J. Chem. (1977) 71, 10; 1413) which is converted to the corresponding aldehyde (E). The latter is then treated in same way as in Method 2 above to give the desired analogue (C).

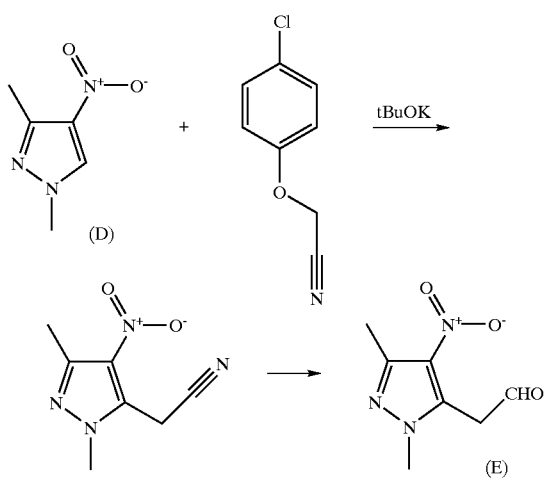

(D)

(E)

Method 4

Starting compound (F) is subjected to a Michael type addition as shown in the reaction scheme below (Izv. Akad. Nauk SSSR, Ser. Khim. 1990 (9), 2089–2093) to give the intermediate (G) which is then reacted with a suitable amine to give the desired analogue (C).

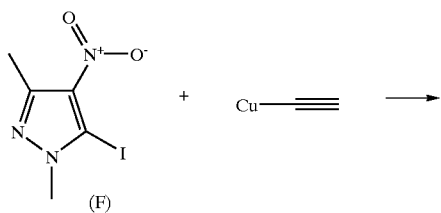

(F)

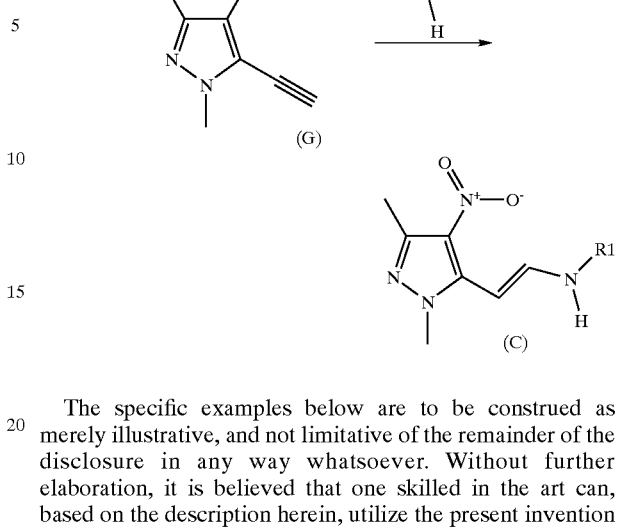

(G)

(C)

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Experimental

The following compounds were used in the Examples below:

Compound A: 4-chloro-2-{[(E)-2-(1,3-dimethyl-4-nitro-1H-pyrazol-5-yl)ethenyl]amino}phenol (formula I wherein $R_1$ and $R_2$ are each $CH_3$, $R_3$ is 5-Cl and $R_4$ is 2-OH).

Compound B: 4-fluoro-1-{[(E)-2-(1,3-dimethyl-4-nitro-1H-pyrazol-5-yl)ethenyl]amino}benzene (formula I wherein $R_1$ and $R_2$ are each $CH_3$, $R_3$ is 4-F and $R_4$ is H).

Compound C: 4-trifluoromethoxy-1-{[(E)-2-(1,3-dimethyl-4-nitro-1H-pyrazol-5-yl)ethenyl]amino}benzene (formula I wherein $R_1$ and $R_2$ are each $CH_3$, $R_3$ is 4-$OCF_3$ and $R_4$ is H).

Compound D: 2,4-dimethoxy-1-{[(E)-2-(1,3-dimethyl-4-nitro-1H-pyrazol-5-yl)ethenyl]amino}benzene (formula I wherein $R_1$ and $R_2$ are each $CH_3$, $R_3$ is 4-methoxy and $R_4$ is 2-methoxy).

These compounds are commercially available and were obtained from the French firm Ambinter, 46 quai Louis Bleriot, F-75016, Paris.

Example 1

Inhibition of $^{125}$I-GLP-1 Binding to Human Recombinant GLP-1 Receptors

Wheatgerm agglutinin scintillation proximity assay (SPA) beads (500 mg) from Amersham (RPNQ 0001) were diluted into 50 ml of assay buffer (Assay buffer consisted of 150 mM NaCl, 10 mM $MgCl_2$, 1 mM EDTA, and 20 mM HEPES, pH 7.4). The SPA beads were combined (1:1 v/v) with a crude membrane preparation from COS7 cells transfected with the human GLP-1 receptor at a concentration of 30 μg/ml/well. These cells (COShGLPr, clone #16) were grown in Dulbecco's Modified Eagle Medium with high glucose (DMEM Gibco, #11965-092) supplemented with 10% heat-inactivated fetal bovine serum (Gibco, #1600-044), 2 mM L-Glutamine (Gibco #25030-081), and 10 μg/ml Gentamicin (Gibco #15710-064) with 705 µg/ml Geneticin (G418 sulfate, Gibco) (DMEM complete). The mixture was incubated for two hours at room temperature with constant rotation. The free membranes were washed away by centrifuging the mixture for 5 minutes at 800 rpm in a table-top GLCl (Sorvall) centrifuge. The supernatant was discarded and the pellet was resuspended in 50 ml assay buffer+0.1% bovine serum albumin. Aliquots of 100 µl of the membranes containing 1 mg SPA beads were placed into a well of a 96-well microtiter plate (WALLAC 1450-501). Compound A was dissolved in DMSO to give a 5 mM solution that was further diluted in assay buffer. Aliquots of 50 µl from each dilution were added to wells containing SPA beads. GLP-1 (7–36) amide (Sigma) was added to the wells at 10 µM final concentration for wells to measure non-specific binding. Finally, 50 µl of $^{125}$I-GLP-1 (Amersham IMQ0284; 1600–2000 Ci/mmol; 46000 to 50000 cpm/well). The plate was sealed and incubated in a shaker for 1 h at room temperature. The plates were counted approximately 10 h later in a Microbeta Trilux liquid scintillation counter (WALLAC). The concentrations causing 50% inhibition of binding were estimated by non-linear regression to a one-site binding model. Binding constants ($K_i$) were calculated with the Cheng-Prushoff equation (Cheng Y C and Prushoff W H, Biochem Pharmacol 22:3099, 1973). The results are shown in FIG. 1. As appears therefrom, increasing concentrations of compound A inhibited the binding of GLP-1 to its receptor with a $K_1$ value of approximately 1 µM.

Example 2

Inhibition of GLP-1 Induced cAMP Signaling

GLP-1 signaling was measured in RIN-m5F insulinoma cells, which possess endogenous GLP-1 receptor coupled to adenylate cyclase (Göke R. et al., Mol Cell Endocrinol 85:C39-C44). The cells were obtained from the American Type Culture Collection (ATCC, #203641 F13132) and grown in RPMI 1640 (GIBCO, #21870-076) supplemented with 2 mM L-glutamine, 10% heat inactivated fetal bovine serum, and 10 µg/ml Gentamicin.

Figure 2:
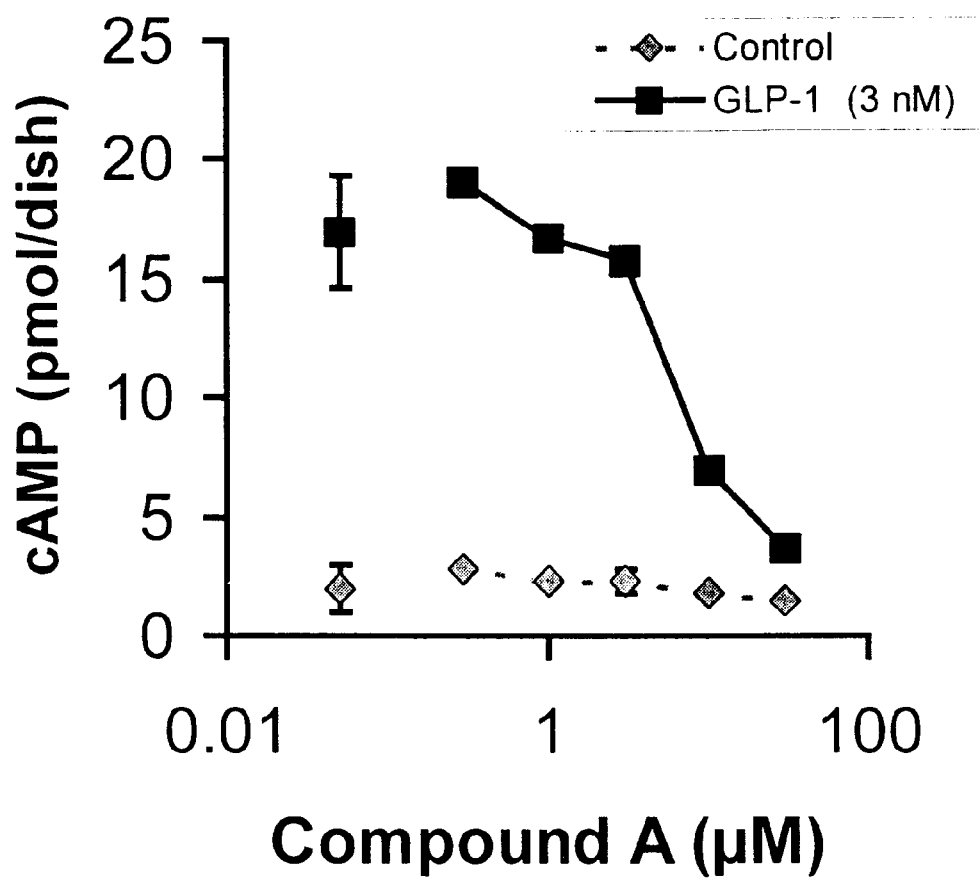
FIG. 2 is a diagram showing cAMP production (pmol/dish) vs. antagonist concentration (microM) during stimulation of RINm5F cells with 3 nM GLP-1.

RIN-m5F cells were plated in 12 well plates at a density of $2.0 \times 10^5$ cells per ml and grown for 4 days in complete RPMI 1640 with 10% fetal bovine serum; the medium was changed the day before experiment. The cells were from 70–90% confluent at the time of the experiment. On the day of the experiment, the incubation medium was removed and the cells were washed with fresh serum-free RPMI 1640 containing 0.1% bovine serum albumin (serum-free medium). One ml DMEM complete with 1 mM 3-isobutyl-1-methylxanthine (Sigma) was added and the plates were placed at 37° C. and 5.0% $CO_2$ for 15 minutes before initiation of the experiment. Fresh compounds were acquired and dissolved as 10 mM solutions in DMSO. A further 1:10 dilution was prepared in DMEM and after the incubation period, the compounds were added to the wells at 30 µM final concentration. The final concentration of DMSO was always 0.3%. The wells were treated with or without GLP-1 (3 nM). The plates were then incubated at 37° C. and 5.0% $CO_2$ for 15 minutes. The medium was removed and cells were washed twice with 1 ml "cold DMEM no serum". For lysis of the cells, 0.5 ml of the 50 mM HCl solution was added to each well and let stand on ice for 1 hour. The solution was mixed well and quantitatively transferred to microcentrifuge tubes with 1 wash of 0.5 ml of the 50 mM NaOH solution. The neutralized cell extracts were centrifuged for 15 min at 15,000 rpm at 4° C. (Tomy centrifuge). The supernatants were transferred to microcentrifuge tubes and the cellular debris was discarded. An aliquot was diluted with cAMP assay buffer and 100 µl was assayed in duplicate in cAMP SPA system (dual range) from Amersham (RPA 538) using the protocol for cAMP concentrations between 0.2 and 12.8 pmol/well as outlined by the manufacturer. The results are shown in FIG. 2. As appears therefrom, compound A concentration dependently decreased GLP-1 stimulated cAMP production to a level close to that obtained in the absence of GLP-1.

Example 3

Inhibition of GLP-1 Stimulated Insulin Release

Figure 3:
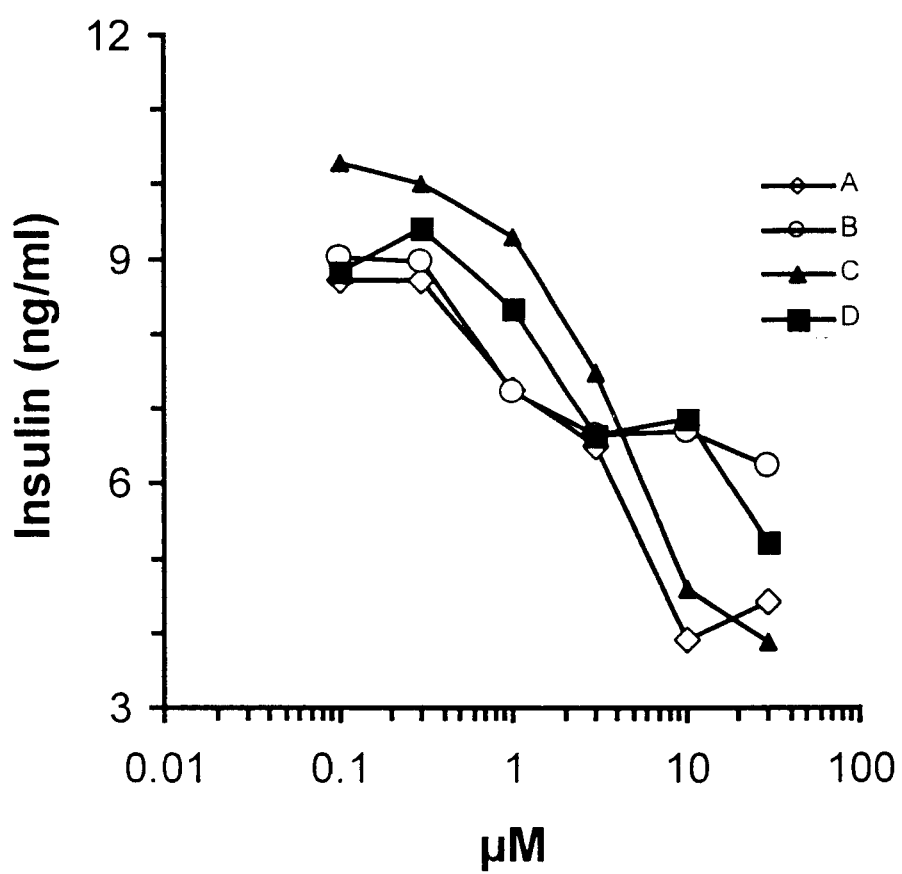
FIG. 3 is a diagram showing insulin release (ng/ml) vs. antagonist concentration (microM) during stimulation of RIN-m5F cells with 3 nM GLP-1 in the presence of four different antagonists.

The RIN-m5F cells were grown as in Example 2. The cells were plated in 96-well plates (10,000 per well) at a density of $2 \times 10^5$ cells per ml and grown for 3 days. The culture medium was changed the day before the experiment. On the day of the experiment, the medium was removed and replaced with serum-free RPMI 1640 containing 0.1% bovine serum albumin (serum-free medium). Dilutions of compounds prepared in serum-free medium from 10 mM DMSO stock solutions to give final concentrations from 0.1 µM to 30 µM were added. The cells were stimulated with 3 nM GLP-1 in a total volume of 200 µl for 1 h and the concentration of insulin in the medium was measured in an ELISA (Mercodia AB). The insulin release in the presence of medium was $6.3 \pm 1.4$ ng/ml and $10.5 \pm 1.4$ ng/ml in the presence of 3 nM GLP-1. The results (mean of triplicate cultures in one experiment) are shown in FIG. 3. As appears therefrom, increasing concentrations of compound A, B, C, or D each causes a substantial reduction of the GLP-1 induced insulin release, i.e. that the compounds effectively antagonise the activity of GLP-1.

What is claimed is:

1. A method of antagonizing GLP-1 activity in a mammalian subject, comprising administering to said subject an effective amount of a compound of the general formula I:

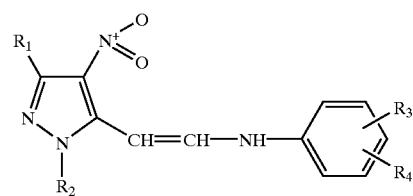

wherein
R$_1$ and R$_2$ independently of each other are C$_{1-4}$alkyl,
R$_3$ is halogen, hydroxy, C$_{1-4}$-alkoxy or trifluoromethoxy,
R$_4$ is hydrogen, hydroxy or C$_{1-4}$-alkoxy,
or a pharmacologically acceptable salt thereof.

2. The method according to claim 1, wherein R$_1$ and R$_2$ are methyl.

3. The method according to claim 1, wherein R$_3$ is halogen, hydroxy, methoxy or trifluoromethoxy.

4. The method according to claim 1, wherein R$_4$ is hydrogen, hydroxy or methoxy.

5. The method according to claim 1, wherein halogen is fluoro or chloro.

6. The method according to claim 3, wherein halogen is fluoro or chloro.

7. The method according to claim 1, wherein the compound is:
4-chloro-2-{[(E)-2-(1,3-dimethyl-4-nitro-1H-pyrazol-5-yl) ethenyl]amino}phenol;

4-fluoro-1-{[(E)-2-(1,3-dimethyl-4-nitro-1H-pyrazol-5-yl)ethenyl]amino}benzene;
4-trifluoromethoxy-1-{[(E)-2-(1,3-dimethyl-4-nitro-1H-pyrazol-5-yl)ethenyl]amino}benzene; or
2,4-dimethoxy-1-{[(E)-2-(1,3-dimethyl-4-nitro-1H-pyrazol-5-yl)ethenyl]amino}benzene.

8. The method according to claim 1, wherein the compound is:
4-chloro-2-{[(E)-2-(1,3-dimethyl-4-nitro-1H-pyrazol-5-yl)ethenyl]amino}phenol.

9. The method according to claim 1, wherein GLP-1 is anatgonized to treat a disease selected from postprandial reactive hypoglycemia, anorexia, reduced intestinal motility and constipation, and Alzheimer's disease.

10. A pharmaceutical composition comprising a compound of formula I in claim 1 and optionally a pharmaceutically acceptable carrier.

11. A method of treating a disorder where inhibition of GLP-1 activity is indicated, the method comprising administering to a mammal subject in need thereof an effective amount of a compound of formula I in claim 1.

12. The method according to claim 11, wherein the disorder is postprandial reactive hypoglycemia.

13. The method according to claim 11, wherein the disorder is anorexia.

14. The method according to claim 11, wherein the disorder is reduced intestinal motility and constipation.

15. The method according to claim 11, wherein the disorder is Alzheimer's disease.

16. The method according to claim 11, wherein the mammal subject is a human.

17. A method of treating a disorder where inhibition of GLP-1 activity is indicated, the method comprising administering to a mammal subject in need thereof a pharmaceutical composition, wherein the pharmaceutical composition comprises an effective amount of a compound of formula I in claim 1 and a pharmaceutically acceptable carrier.

18. A method of inhibiting GLP-1 activity, comprising administering to a mammal subject in need thereof an effective amount of a compound of formula I in claim 1.

19. A method of inhibiting GLP-1 activity, comprising administering to a mammal subject in need thereof a pharmaceutical composition, wherein the pharmaceutical composition comprises an effective amount of a compound of formula I in claim 1 and a pharmaceutically acceptable carrier.

20. The method according to claim 1, wherein $R_4$ is hydroxy or $C_{1-4}$-alkoxy.

* * * * *